US006459934B1

United States Patent
Kadhiresan (10) Patent No.: US 6,459,934 B1
(45) Date of Patent: Oct. 1, 2002

(54) ESTIMATE OF EFFICIENCY USING ACCELERATION-HEART RATE RATIO

(75) Inventor: Veerichetty Kadhiresan, Temecula, CA (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 09/621,389

(22) Filed: Jul. 21, 2000

(51) Int. Cl.$^7$ .............................................. A61N 1/362
(52) U.S. Cl. ............................ 607/9; 600/510; 600/520
(58) Field of Search ................................. 600/508–510, 600/513, 519–520, 483, 526, 587; 607/3, 9, 17–19

(56) References Cited

U.S. PATENT DOCUMENTS

| | | | | |
|---|---|---|---|---|
| 5,125,412 A | * | 6/1992 | Thorton | 600/484 |
| 5,154,170 A | | 10/1992 | Bennett et al. | |
| 5,360,436 A | | 11/1994 | Alt et al. | |
| 5,976,083 A | * | 11/1999 | Richardson | 600/300 |
| 6,021,351 A | | 2/2000 | Kadhiresan et al. | |
| 6,058,329 A | * | 5/2000 | Salo et al. | 607/17 |
| 6,190,324 B1 | * | 2/2001 | Kieval et al. | 600/483 |

OTHER PUBLICATIONS

Evaluation of Commerical Accelerometer (Tritrac–R3 D) to Measure Energy Expenditure During Ambulation *International Journal of Sports Medicine* (vol. 19, Jan. 1998, pp. 43–47).

Ability of the Caltrac Accelerometer to Access Daily Physical Activity Levels *Journal of Cardiopulmonary Rehabilitation* (vol. 15, Mar./Apr. 1995, pp. 107–113).

Improving Energy Expenditure Estimation by Using a Triaxial Accelerometer *Journal of Applied Physiology* (vol. 83, No. 6, Dec. 1997, pp. 2112–2122).

Assessment of Energy Expenditure for Physical Activity Using a Triaxial Accelerometer *Medicine & Science in Sports & Exercise* (vol. 26, No. 12, Dec. 1994, pp. 1516–1523).

J.K. Moon Et Al: "Combined heart rate and activity improve estimates of oxygen consumption and carbon dioxide production rates" Journal of Applied Physiology, vol. 81, No. 4, 1996, pp 1754–1761, XP002183916

Moon Et Al.: "Prediction of oxygen consumption rates from heart interval mean and variance" Engineering in Medicine and Biology Society, 1995. IEEE 17$^{th}$ Annual Conference Montreal, Que., Canada Sep. 20–23 1995, New York, NY, USA, IEEE, US, Sep. 20, 1995, pp 725–726, XP010215591 ISBN: 0–7802–2475–7.

* cited by examiner

Primary Examiner—Kennedy Schaetzle
Assistant Examiner—Kristen Droesch
(74) Attorney, Agent, or Firm—Nikolai & Mersereau, P.A.; Thomas J. Nikolai (57) ABSTRACT

A method for estimating the efficiency of a patient's body, and specifically for estimating the efficiency of a patient's body while undergoing different cardiac therapies. Acceleration and heart rates of the patient are measured while undergoing various therapies. The acceleration—heart rate ratio for each therapy is calculated. The ratios for each therapy are compared and the therapy that has the highest acceleration—heart rate ratio is determined to be the most efficient. The most efficient therapy allows the patient to have the most acceleration with the lowest corresponding heart rate.

17 Claims, 10 Drawing Sheets

ESTIMATE OF EFFICIENCY USING ACCELERATION-HEART RATE RATIO

BACKGROUND OF THE INVENTION

I. Field of the Invention

This invention relates generally to a method and apparatus for assessing the efficiency of a patient's body. More particularly, the present invention relates to a method and apparatus for estimating the efficiency of the body of a patient suffering from chronic congestive heart failure (CHF) while undergoing different cardiac therapies, in order to determine the best therapy for the patient. The efficiency of a patient's body while undergoing a therapy can be determined by measuring and calculating the patient's acceleration—heart rate ratio while undergoing the therapy. More than one type of therapy can be performed on a patient and the acceleration—heart rate ratios, or efficiency indices, of the therapies can be compared to determine the best cardiac therapy for the patient.

II. Description of the Related Art

The heart muscle derives its energy almost entirely from aerobic metabolism, which means it consumes oxygen. A healthy heart requires less oxygen, or uses less energy, than an unhealthy heart does to achieve a given cardiac output.

Heart rate is an important determinant of myocardial oxygen and energy consumption. The energy cost per minute of the heart must equal the energy cost per beat times the number of beats per minute. Effectively, a more efficient heart has a lower corresponding heart rate for any given stroke volume.

For CHF patients especially, it is important to maintain a low heart rate, thereby reducing the energy demand of the heart. Heart rates of CHF patients are artificially kept low by using drugs such as beta-blockers. However, CHF patients typically manifest abnormally low cardiac output as a result of their condition. In order to still get an adequate amount of blood flow to the body of these patients, pacing therapy has been used. Implantable cardiac rhythm management devices have been used to enhance hemodynamic performance of the heart by pacing the left ventricle and appropriately setting the atrial-ventricular delay (AVD) parameter. However, it is unclear the effect that pacing therapy has on the heart rate of CHF patients.

Attempts have been made to develop clinically practical methods for estimating energy expenditure during various activities. Several studies have used accelerometers, which measure body movement, to estimate total body energy expenditure of the patient during specific laboratory exercise tests or daily life activities. Some articles detailing such studies include: "Evaluation of Commercial Accelerometer (Tritrac-R3 D) to Measure Energy Expenditure During Ambulation" in the International Journal of Sports Medicine (Vol. 19, January, 1998, pp. 43–47); "Ability of the Caltrac Accelerometer to Assess Daily Physical Activity Levels" in the Journal of Cardiopulmonary Rehabilitation (Vol. 15, March/April, 1995, pp. 107–113); and "Improving Energy Expenditure Estimation by Using a Triaxial Accelerometer" in the Journal of Applied Physiology (Vol. 83, No. 6, December, 1997, pp. 2112–2122). One such study, in particular, as detailed in "Assessment of Energy Expenditure for Physical Activity Using a Triaxial Accelerometer" in Medicine & Science in Sports & Exercise (Vol. 26, No. 12, December 1994, pp. 1516–1523), found a high correlation (r=0.96) between energy expenditure and acceleration in the antero-posterior direction during walking. The study indicated that it was possible to obtain an estimate of energy expenditure from acceleration measurements.

A method is still needed that will allow physicians to determine whether a patient's body is efficient or not during activity. A high level of activity with a corresponding low heart rate indicates efficiency. In particular, a method is needed that will allow a physician to determine the efficiency of a patient's body while the patient undergoes different cardiac therapies, and thereby determine the best therapy for the patient. The inventive method and apparatus allow for identification of the best cardiac therapy for a patient.

After considering the related art, it can be seen that a need exists for a method and apparatus to determine the efficiency of a patient's body while undergoing certain cardiac therapies, and, in particular, the efficiency of a CHF patient's body. The present invention meets the need for such a method and apparatus. It uses an accelerometer to measure the activity of a patient, which, as the prior art indicates, establishes the level of energy that is expended by a patient during the activity. The invention also measures the heart rate of a patient over time. The ratio of acceleration and heart rate is then calculated for each cardiac therapy performed on the patient. The acceleration—heart rate ratios for the tested therapies are then compared to determine which cardiac therapy is the best for the patient. The best therapy will be the one that allows the most acceleration, or activity, with the lowest corresponding heart rate. The best therapy will have the highest acceleration heart rate ratio, otherwise called the "efficiency index." Overall, the described method and apparatus meet the existing need for the invention.

SUMMARY OF THE INVENTION

In its simplest embodiment, the invention comprises measuring the values of acceleration and heart rate for a patient, and calculating the ratio of acceleration to heart rate. The ratio is the patient's efficiency index. The invention may also be used to evaluate the effect of different cardiac therapies on the patient, by measuring acceleration and heart rate values during cardiac therapies and by calculating the acceleration—heart rate ratio that correspond to the therapies. The ratios may be compared, and the therapy with the highest acceleration—heart rate ratio, or efficiency index, is determined to be the best therapy for the patient. The best therapy is the one that allows the patient to have the most acceleration, or activity, with the lowest corresponding heart rate.

BRIEF DESCRIPTION OF THE DRAWINGS

The foregoing objects and advantages of the present invention will become apparent to those skilled in the art from the following detailed description of the preferred embodiment, especially when considered in conjunction with the accompanying drawings in which.

DETAILED DESCRIPTION OF THE PREFERRED EMBODIMENT

The present invention represents a method and apparatus for estimating the efficiency of a patient's body. Specifically, the method and apparatus can be used to estimate the efficiency of the body of a patient without any therapy being used and also while the patient is undergoing different cardiac therapies. This is done by measuring and calculating the patient's acceleration—heart rate ratios either without any therapy or while undergoing the different therapies. The ratios are then compared to determine which therapy, if any, is the best for the patient. The embodiment detailed herein is intended to be taken as representative or exemplary of those methods or apparatuses that may be used to estimate the efficiency of a patient's body and is not intended to be limiting.

In implementing the method, an accelerometer is needed to detect the body movement or activity of the patient. The accelerometer may be an external device that is taped to the patient's chest or, alternatively, may comprise an accelerometer of a type that is built into an implantable cardiac rhythm management device. (See FIG. 1). The accelerometer may be a piezoelectric or a piezoresistive device, which produces a raw accelerometer output signal proportional to body movement.

The heart rate of the patient is measured by microprocessor circuitry controlling the pulse generator of an implantable cardiac rhythm management device, if the patient has one. (See FIG. 1). Otherwise, the heart rate can be measured by the surface electrodes of an electrocardiogram (ECG) or other monitoring device.

Figure 1:
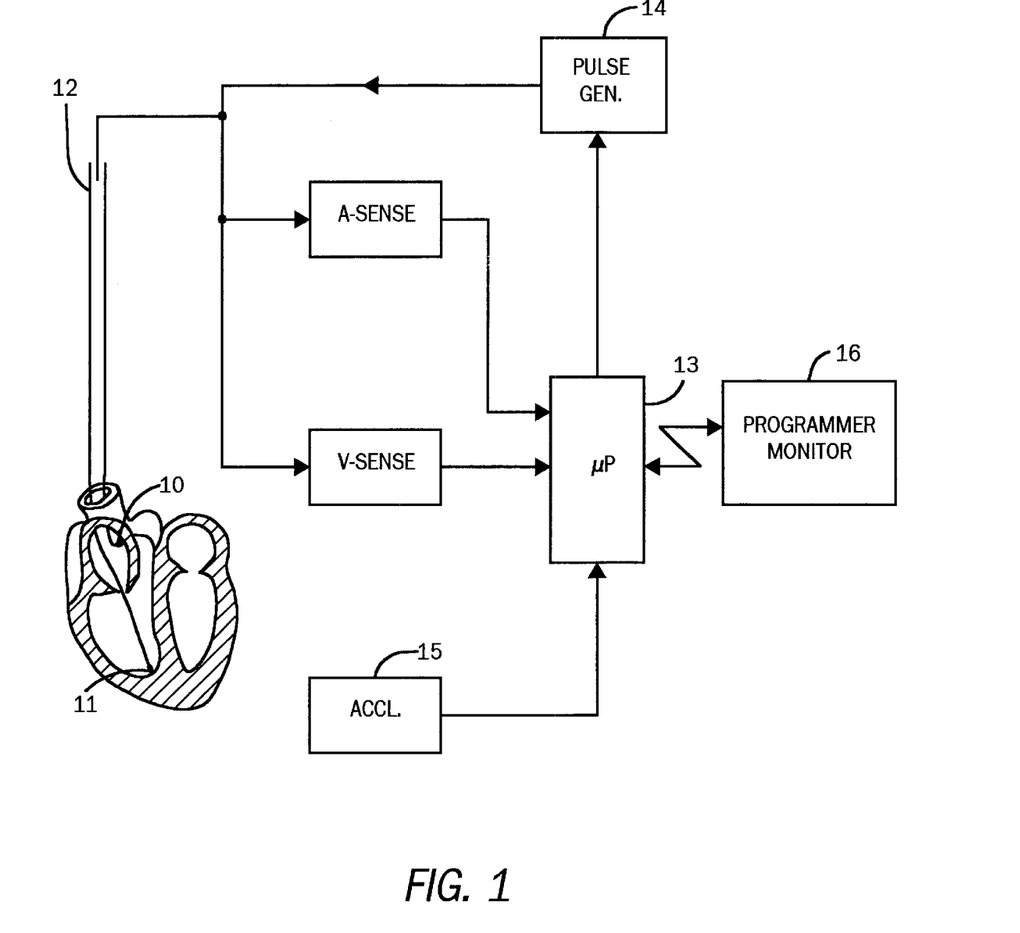
FIG. 1 is a schematic block diagram of one example implementation of the inventive apparatus, which is incorporated into an implantable cardiac rhythm management device.

FIG. 1 is a schematic block diagram of an implantable cardiac rhythm management device. This device is one implementation of the apparatus that can carry out the inventive method. Parts of the implantable cardiac rhythm management device are the atrial 10 and ventricular 11 pacing electrodes that sense the P-waves and R-waves. The pacing lead 12 delivers the data from the electrodes to a microprocessor 13, which stores the data and is able to compute results that may signal the pulse generator 14 of the implantable cardiac rhythm management device to change its pace. The microprocessor 13 can also compute heart rate from the R-wave to R-wave interval. If a patient has an accelerometer 15, the output from it can be signal processed to develop a raw accelerometer signal that is proportional to the patient's activity. These data are also delivered to the microprocessor 13. The microprocessor 13 is then able to compute the acceleration—heart rate ratio. The results can be displayed on a programmer monitor 16.

The inventive method may be used to determine the efficiency of a patient's body while undergoing a certain cardiac therapy. It does not have to be used to compare a plurality of therapies. If just one therapy is to be evaluated using the inventive method and apparatus, a monitoring protocol needs to be defined including the type of cardiac therapy that is to be used on the patient and the total time period during which the efficiency is to be determined. The values of acceleration and heart rate of the patient are then measured during the total time period of the therapy. The acceleration—heart rate ratio is calculated from the measured values, which is an index of the efficiency of the patient's body while undergoing the cardiac therapy. The ratio, or efficiency index, could then be compared to the ratio of the patient without undergoing any therapy to determine whether the therapy makes the patient's body more efficient or not.

Figure 2:
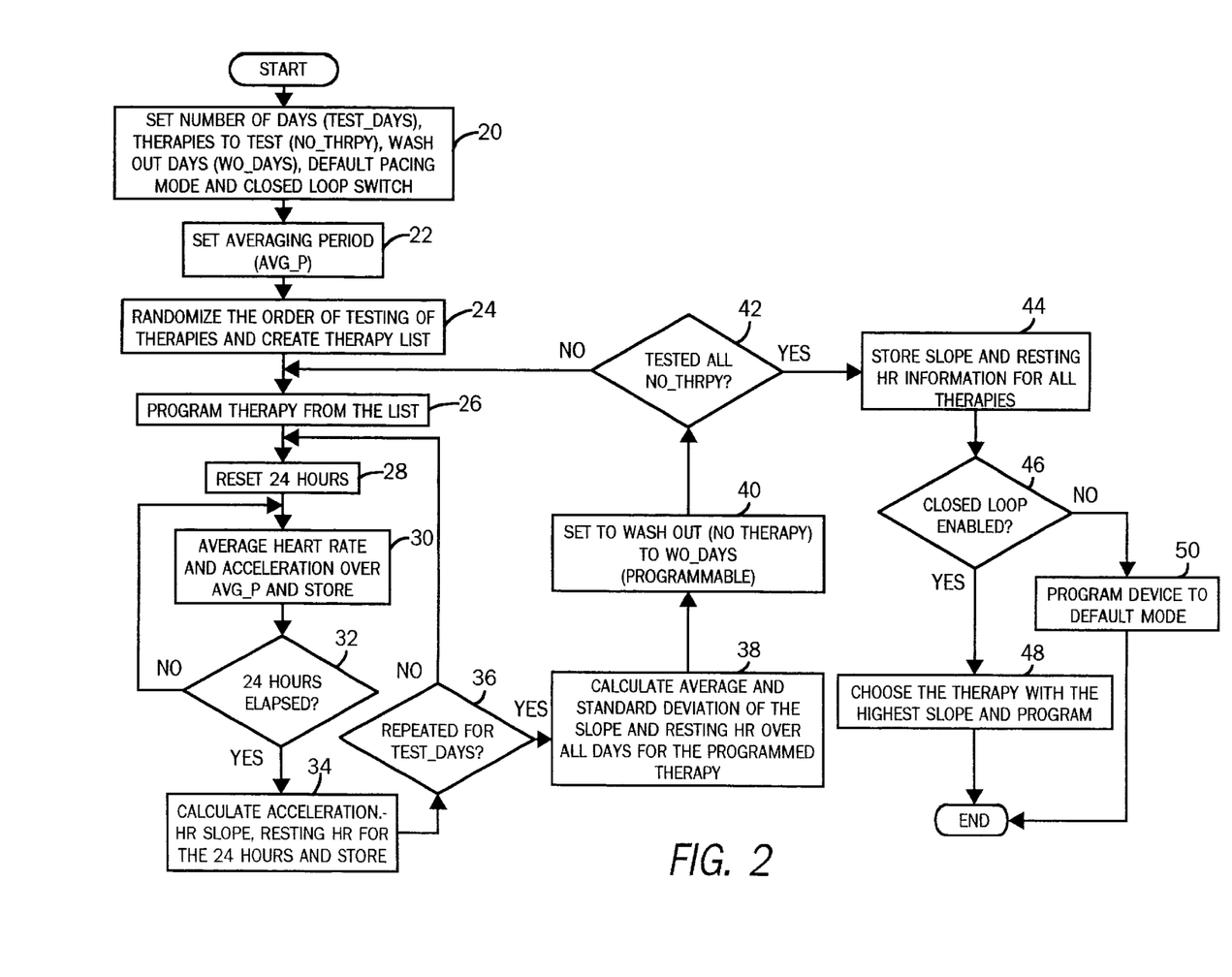
FIG. 2 is a flow diagram of one example implementation of the inventive method.

Referring to FIG. 2, there is illustrated by means of a flow diagram another possible implementation of the method used to estimate the efficiency of a patient's body. This implementation involves the patient undergoing different cardiac therapies during the total time period of testing, which are ultimately compared by their efficiency indices. The first step of the flow diagram, as illustrated, is to establish the monitoring protocol, which includes defining the number of days that each therapy will be tested (TEST_DAYS), the different types of therapies that will be tested (NO_THRPY), the wash-out period (WO_DAYS) between the therapies that are tested, the default pacing mode, and the closed loop switch. (See Block 20).

This invention does anticipate programming the above information into a programmable microprocessor, which is part of the inventive apparatus. However, programming the information into the microprocessor is not absolutely required, and the invention is not limited to only programming the protocol into a microprocessor.

The number of days (TEST_DAYS) is part of the total time period of the testing of the patient. This period of time is a first time period within the total time period. In the preferred embodiment, the first time period, or TEST_DAYS, is twenty-eight (28) days. Without intending to limit the invention, the number of days that each therapy is tested may be any amount as long as it is sufficiently long enough to allow the pacing to have an effect on the patient. Regardless of the number of test days that are used to test a given therapy, the same period of time should be used to test all of the therapies.

There are many different types of pacing therapies (NO_THRPY) that may be tested on a patient. The different types of cardiac pacing therapy result from varying the pacing sites (e.g. right ventricle (RV), left ventricle (LV) or both ventricles (BV)) and varying the atrial-ventricular delay (AVD) and intra-ventricular delay (IVD) (e.g. AVD of 100 ms, 180 ms, 120 ms or 50 ms, and IVD of 20 ms or 0 ms). The types of these therapies are then also programmed into the programmer.

There are other kinds of therapies that may be used in evaluating a patient that are not pacing therapies. Some examples are different drug therapies. Obviously, these therapies are not able to be programmed into the microprocessor, since they are administered differently than cardiac pacing therapies, which may be programmed into a microprocessor that is part of an implantable cardiac rhythm management device. However, the inventive method is not limited to therapies that may be programmed into an implantable cardiac rhythm management device.

Another part of the monitoring protocol in FIG. 2 is defining or setting the wash-out period (WO-DAYS). The wash-out period is a period of time when no therapy is administered to the patient, which is between periods when therapies are administered. They are used to separate the effects of different therapies on the patient. They can be any number of days that are sufficient to separate the effect of different therapies. Some examples of the lengths of wash-out periods are ten (10) days or twenty-eight (28) days. However, any number of days can be used. The number of wash-out days can also be programmed to be zero (0) if a wash-out period is not needed or wanted.

When the therapies being tested on a patient are pacing therapies, and not drug therapies, there are two additional parts of the monitoring protocol. First, if pacing therapies are tested on the patient, the physician must determine the default mode for the patient. This is the mode that the patient should be in after all the testing is done. The term "mode" may refer to a particular pacing parameter, such as AVD or IVD, or pacing site, such as LV, RV or BV. The default mode can be one of the modes that was tested on the patient or some other mode. Second, when pacing therapies are tested on the patient, a closed loop switch may or may not be used. If the closed loop switch is enabled, the best therapy (the one with the highest acceleration—heart rate ratio) is automatically programmed at the end of the testing period.

Figure 3:
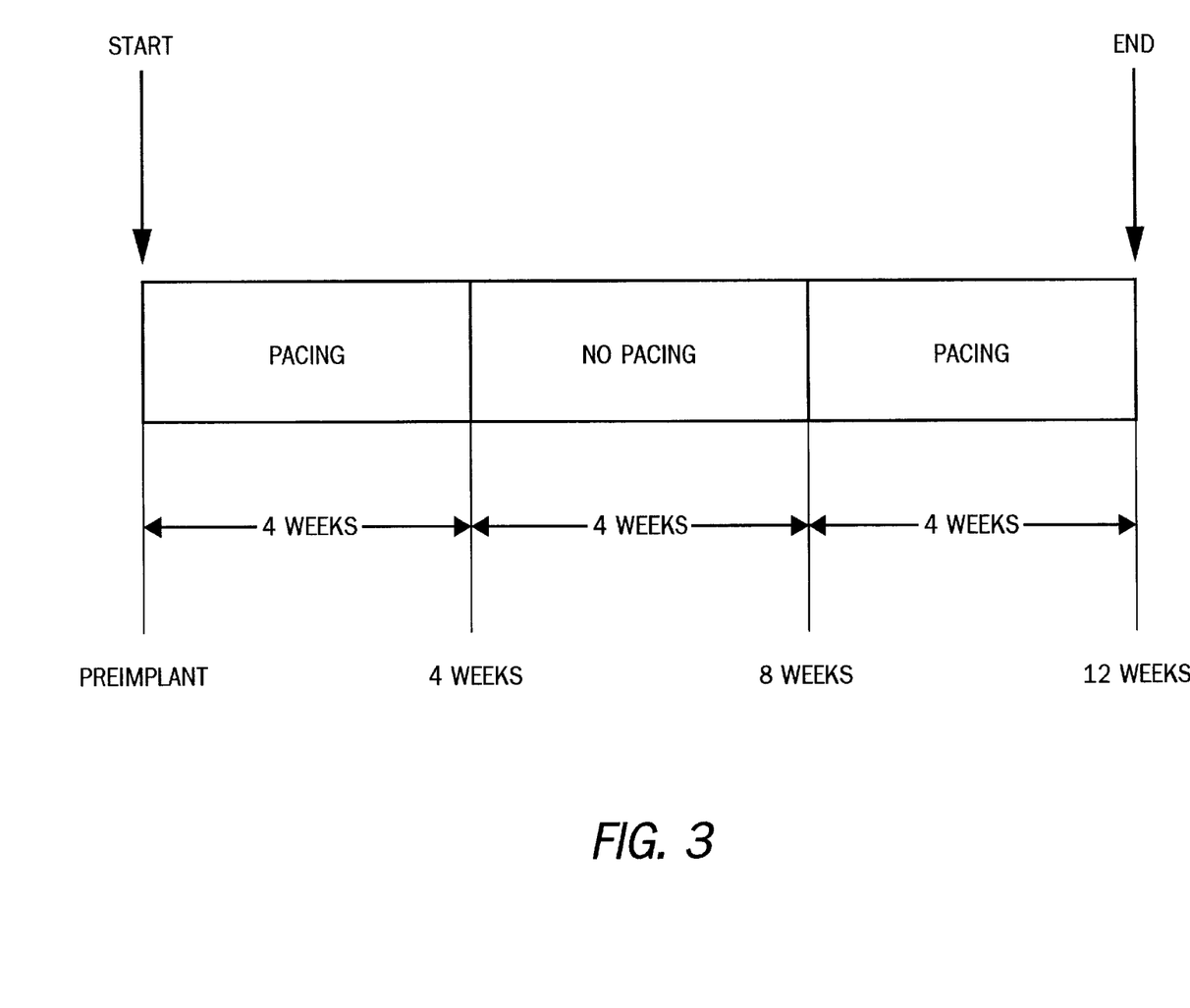
FIG. 3 is a diagram of pacing therapies in congestive heart failure (PATH-CHF) study protocol.

The PATH-CHF Study, performed in the development of this inventive method, used the protocol that is shown in FIG. 3. This protocol included measuring acceleration and heart rates prior to implantation of the implantable cardiac rhythm management device. After implantation of the device, each patient was paced at one site for four (4) weeks under one mode of therapy, which was followed by four (4) weeks of no pacing (the wash-out period). The patient was then paced again under a different mode of therapy for another four (4) weeks. This protocol is used in this inventive method. Alternative protocols with different numbers of testing days, wash-out periods and types of therapies can be used instead.

In order to calculate the efficiency of a patient's body while undergoing a given therapy over a given period of time, the data that are being collected throughout the period need to be averaged over shorter periods of time. The next step in the method (FIG. 2) is to set this averaging period (AVG_P). (See Block 22 in FIG. 2). In the preferred embodiment, the averaging period is five (5) minutes. Therefore, in the preferred embodiment, the acceleration and heart rate data is collected and averaged over 5 minute intervals. As a result, 228 values are collected for each 24 hour period of testing. There is a plurality of second time periods, 5 minute periods in this embodiment, within a first time period, each 24 hour period in this embodiment, of which there is a plurality in the total time period, which is four weeks, or twenty-eight days, in this embodiment. The plurality of second time periods, 5 minute periods, is preferred but not required in the inventive method, as are the other time periods. Alternative times periods can be used, however, they must be kept consistent with regard to each patient in order to compare results of different therapies.

The next step in the preferred embodiment of this inventive method is to randomize the order of the testing therapies and to create a therapy list. (See FIG. 2, Block 24). The next step then is to program or test the first therapy from the list. (See Block 26).

The therapy is performed on the patient for the chosen first period of time, which is twenty-four (24) hours in the preferred embodiment. (See Block 28). This is a suggested time period, however, and can be a different amount of time.

An accelerometer is used to measure the acceleration of the patient during the twenty-four (24) hour, or other, time period. The circuitry of the implantable cardiac management device measures and stores the heart rate and acceleration data collected during the twenty-four (24) hour period. The data stored include the average accelerations (averaged over a period of five minute intervals in the preferred embodiment) and heart rate values of a patient over time (AVG_P), which are the second periods of time in the total time period. (See Block 30).

The accelerometer values are measured in terms of gravitational force (mG). The heart rate values are measured in beats per minute (bpm).

Once the values from each twenty-four hour period are measured (Block 32) and stored, the slope and the intercept between acceleration and heart rate are calculated using the linear least square analysis. (Block 34). A higher order non-linear analysis can also be performed to improve the correlation.

The next step in the method is to continue to collect and analyze data during twenty-four (24) hour increments of time until the predetermined total number of days (TEST_DAYS), or first time period, of the therapy is completed. (Block 36). These values are plotted on a graph of acceleration versus heart rate. (See FIG. 4 for example). A line is then fit to the graph The slope and intercept from each 24 hour period are stored, along with the resting heart rate. The values for each twenty-four hour period in the testing period, which is twenty-eight days in the preferred embodiment, are averaged to determine the average and standard deviation of the slope, or acceleration—heart rate ratio, and the resting heart rate. (Block 38).

The next step in the method is to set the wash-out days (WO_DAYS), if there are any. (Block 40). A wash-out period, during which no therapy is administered, is done before switching to the next therapy. To skip the wash-out period, the WO_DAYS can be set to zero.

After the wash-out period is done, the next step in the method is to test the next chosen therapy and repeat Blocks 28 through 40 for the next therapy or therapies. The determination must be made as to whether all of the chosen therapies (NO_THRPY) have been tested. (See Block 42). Once all of the therapies have been tested, the average slope and resting heart rate information for each of the therapies that was tested is stored. (See Block 44). At that point, if the closed loop switch is used, it is enabled and the therapy that is determined to have the highest acceleration—heart rate ratio (or efficiency index) is automatically programmed. (Blocks 44 and 46). If a closed loop switch is not enabled, the implantable cardiac rhythm management device defaults to the default mode at the end of all of the testing (Blocks 48 and 50). After that time, the physician can review the results and program the device to carry out the most efficient therapy, if it is desired.

The therapy with the highest corresponding average acceleration—heart rate ratio or "efficiency index" is the best therapy for the patient. The best therapy allows the patient to have more acceleration with a lower corresponding heart rate.

The values collected by use of the method and apparatus on a patient can be displayed. One way to display them is on a programmer monitor. They may be displayed in either table or graph form.

Another use for this invention is to calculate the efficiency index, or acceleration—heart rate ratio, for a patient that is not undergoing any cardiac therapy. It can be used to assess the fitness and well being of such a patient.

Yet another use for this method is to determine the necessary pace of the heart of a chronotropically incompetent patient, which is a patient with sinus node dysfunction. A chronotropically incompetent patient's heart rate does not increase over a certain level, even during exercise. In order to use this method to help these patients, the acceleration and heart rates are measured for these patients up to the point that their heart rates no longer increase. These values are plotted and displayed. The physician is then able to extrapolate to find out what the heart rate should be for any desired acceleration. An implantable cardiac rhythm management device in such a patient can then be programmed to increase the heart rate of the patient over its normal upper limit to correspond to the higher levels of acceleration, or activity, of the patient.

EXAMPLES

Investigators at Guidant Corporation (applicant's assignee) undertook the PATH-CHF study, which led to the development of this method. One patient in the PATH-CHF study, Patient #11, had her heart rate and acceleration monitored during four different time periods. The acceleration of Patient #11 was measured by using an external accelerometer that was taped to her chest.

Data were collected during four different periods. (See FIG. 3). The first period was prior to implantation of an implantable cardiac rhythm management device, and was called "preimplant." The second period was the four weeks immediately after the implantable cardiac rhythm management device was implanted. The patient was paced at the left ventricular site at an AVD of 120 ms during this second period. The third period, which was the next four weeks of the study, did not include any pacing. It was the washout period. The pacing was resumed, but in the biventricular mode at an AVD of 120 ms, during the next four weeks of the study, which was the fourth period of time.

Figure 4:
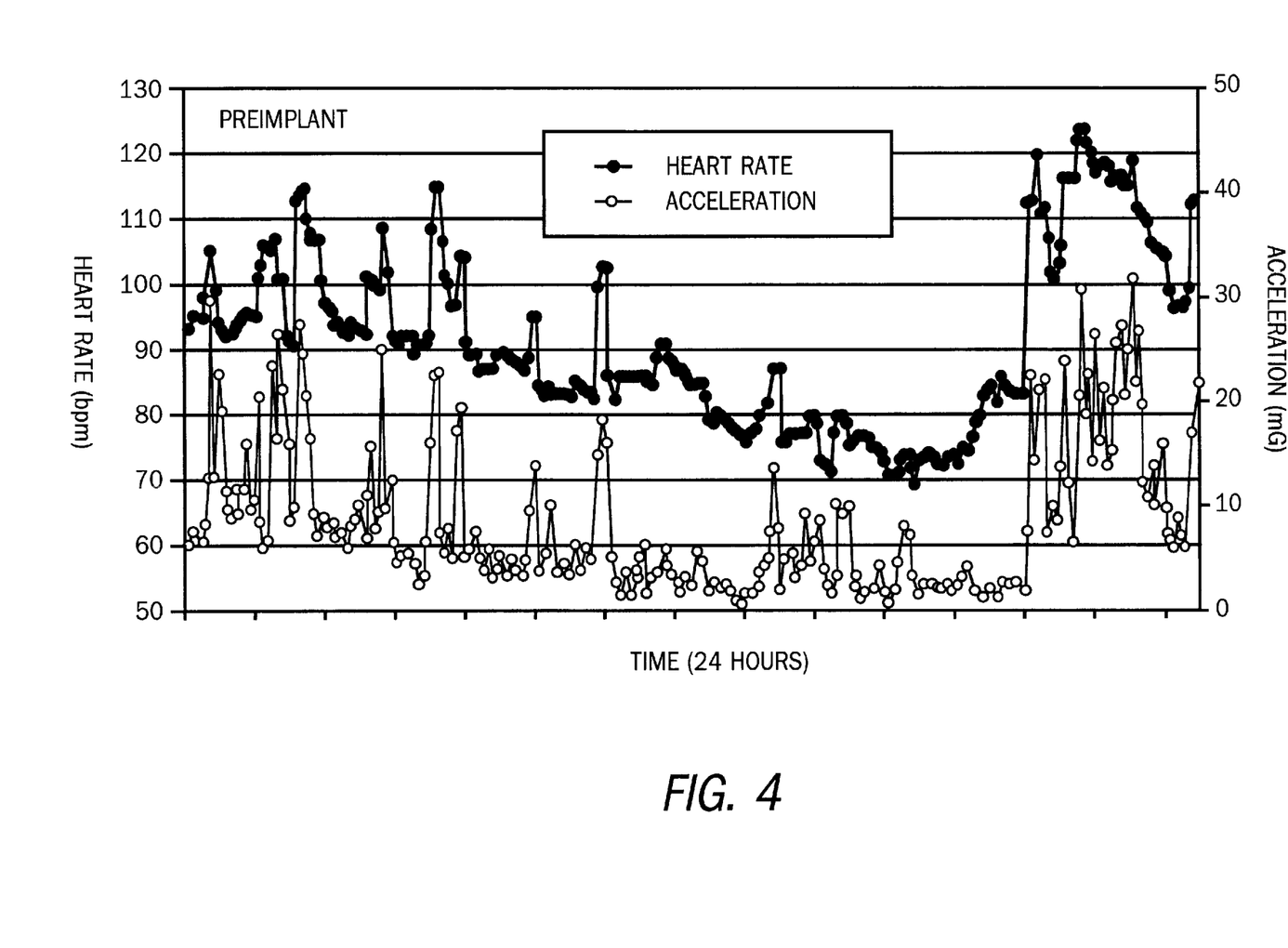
FIG. 4 is a graph of the acceleration and heart rate of Patient #11 during a twenty-four hour period of time during the preimplant period.
Figure 5:
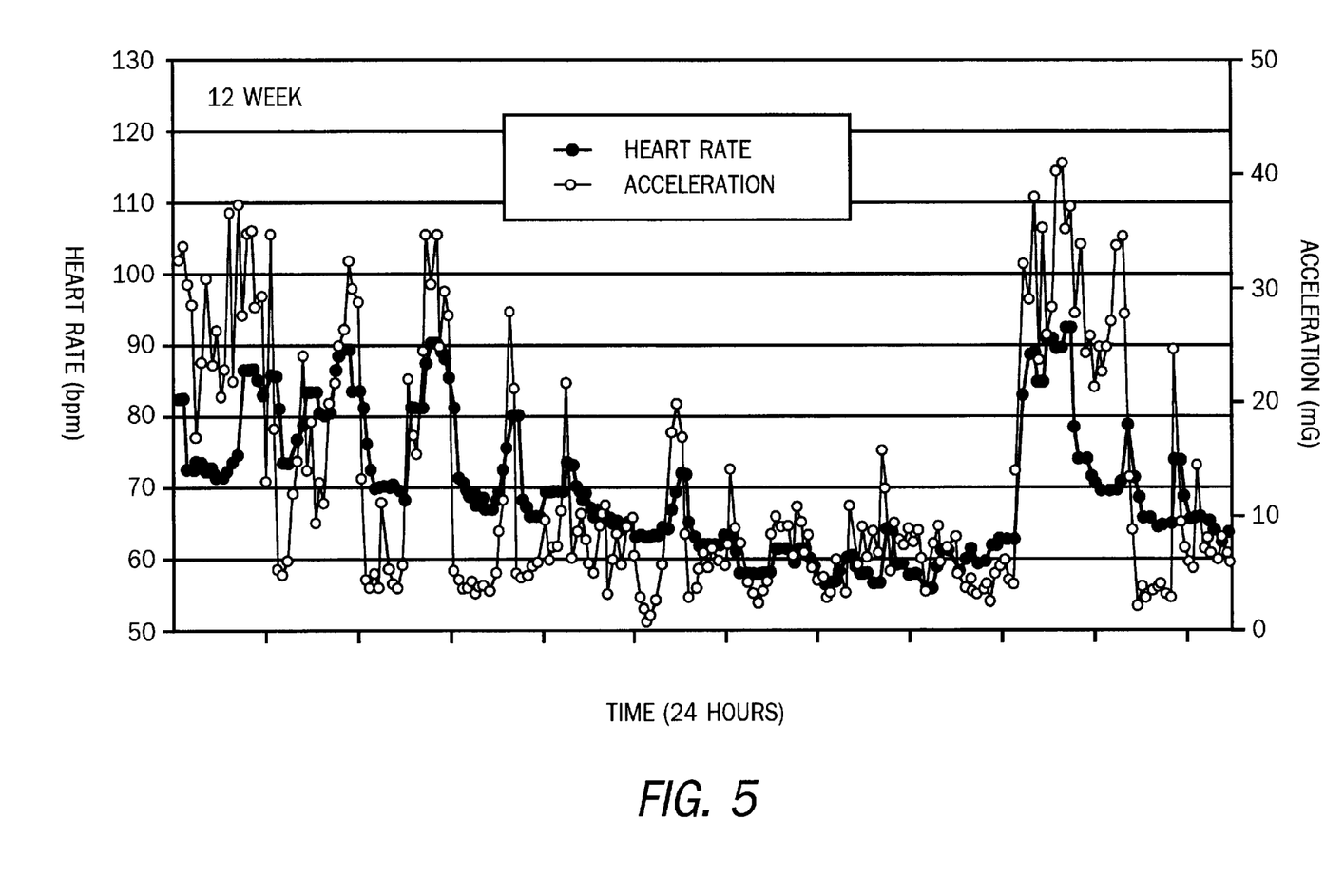
FIG. 5 is a graph of the acceleration and heart rate of Patient #11 during a twenty-four hour period of time during a pacing period.

FIG. 4 shows the graph of acceleration and heart rate over a twenty-four hour period of time for Patient #11 prior to implantation of an implantable cardiac rhythm management device. Meanwhile, FIG. 5 is a graph of the values collected from Patient #11 during a twenty-four hour period of time of pacing therapy. Comparing the results shown in the two figures, it can be seen that, generally, the acceleration—heart rate ratio for the patient was higher during pacing than without pacing. Therefore, the patient's body was more efficient with pacing than without pacing.

Figure 6:
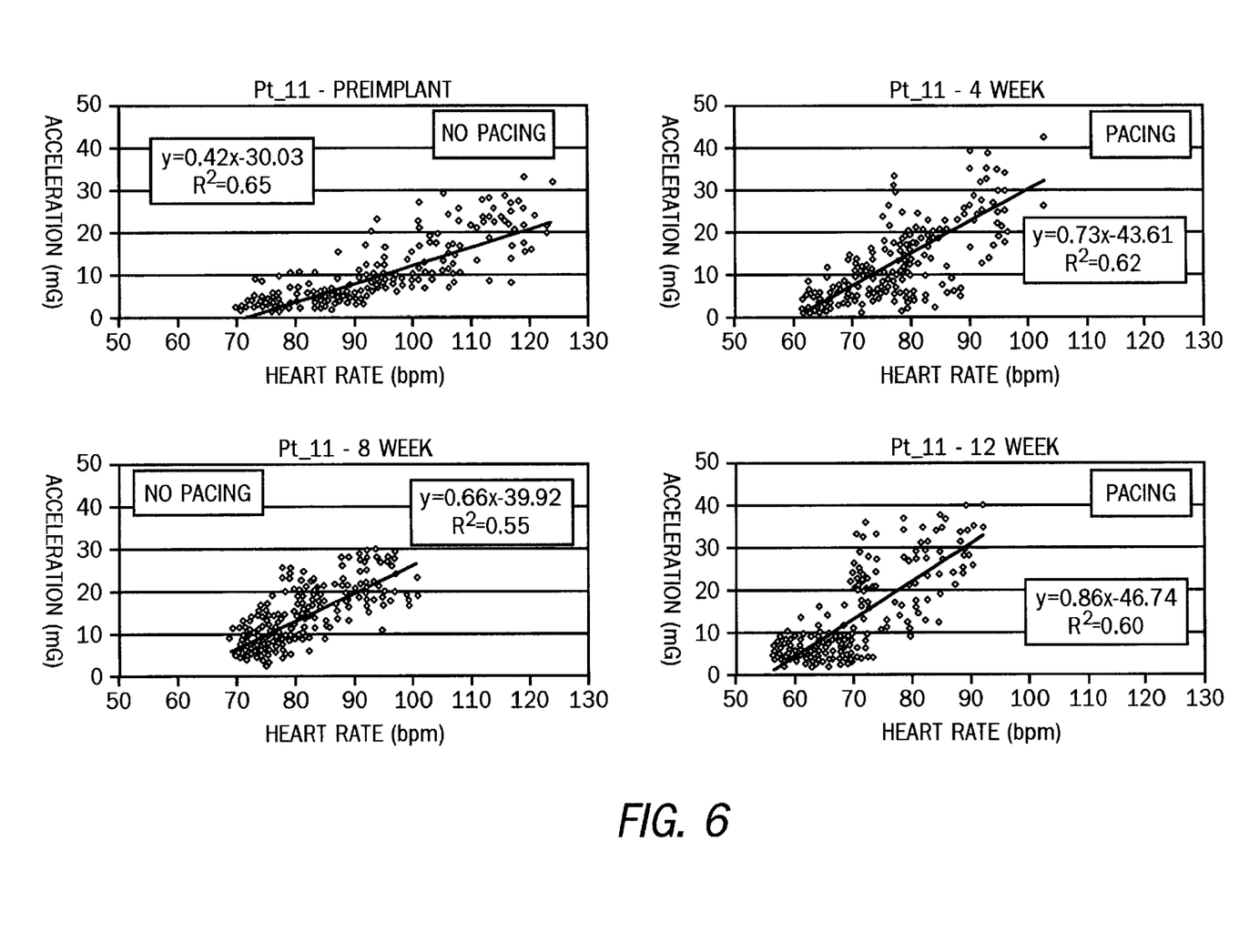
FIG. 6 includes four graphs of the acceleration—heart rate relationships from one twenty-four hour period within each of the four (4) time periods of the PATH-CHF protocol for Patient # 11.

FIG. 6 includes four graphs that show the acceleration—heart rate relationship of Patient #11 during the four different time periods, as described in FIG. 3. The four graphs in FIG. 6 depict values collected during each of the four periods. The plots on the graphs represent the values for each AVG_P, or five minute interval in the 24 hour period. Lines have been fit to the graphs. These four graphs show that the slope, or acceleration—heart rate ratio, is sensitive to the type of therapy being administered. The graphs in FIG. 6 also include the equations for the lines. The higher the slope of the line, the greater the efficiency of the patient's body during the corresponding time period. It can be seen by looking at the four graphs in FIG. 6 that the patient's efficiency index was higher during the periods of pacing, than during no pacing. In particular, compared to the first pacing mode, the slope was higher during the second pacing mode. Therefore, Patient 11's body was more efficient while the patient's heart was being paced in the biventricular mode.

Figure 7:
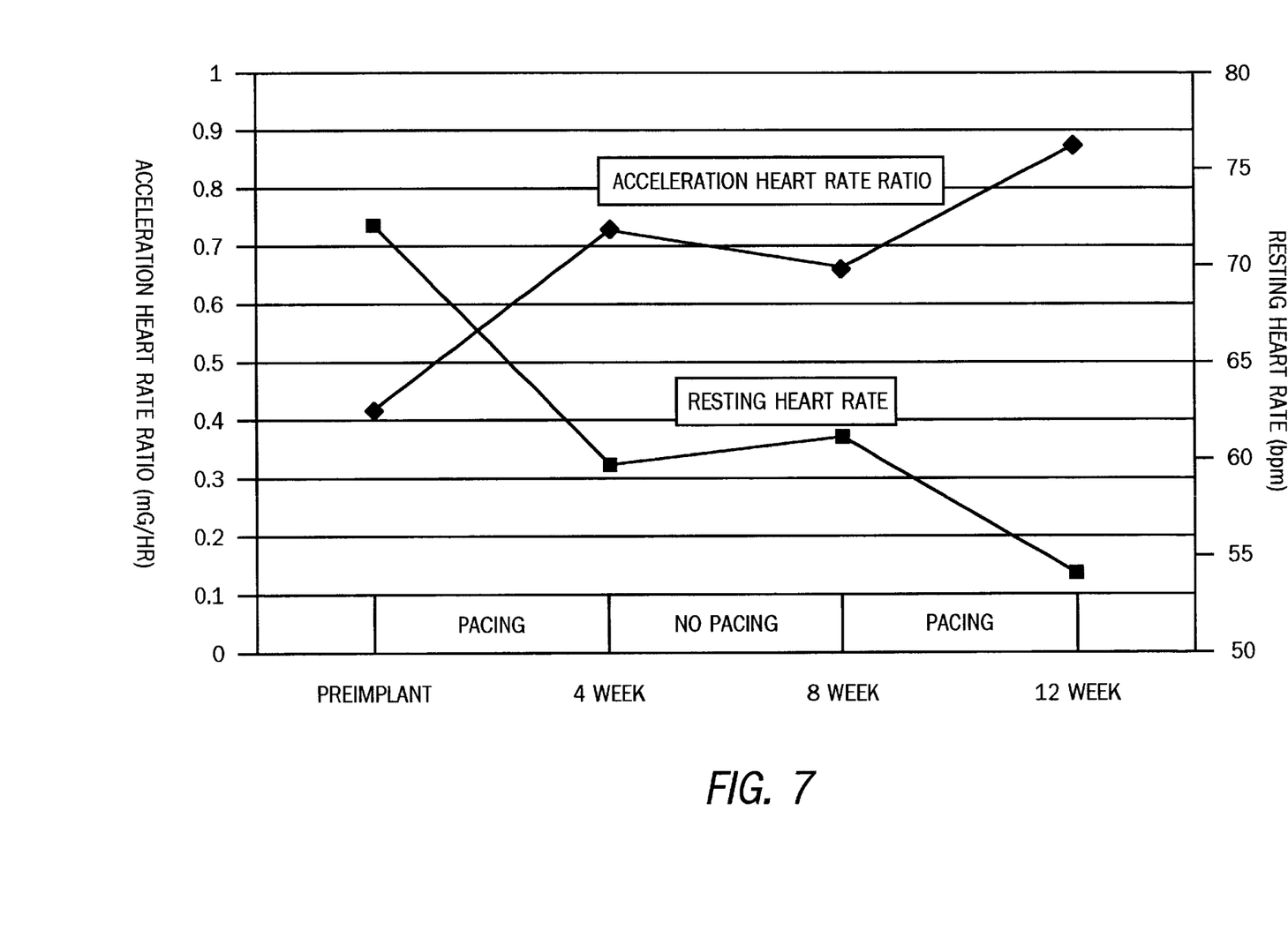
FIG. 7 is a graph of the efficiency index and the resting heart rate of Patient #11 during the protocol.

FIG. 7 shows the efficiency index, or acceleration—heart rate ratio, and resting heart rate averages for Patient #11 for the four different periods of the study. The plots are the average for each of the four time periods of the study, as described and shown in FIG. 3. As can be seen, the resting heart rate of the patient goes down during pacing while the acceleration—heart rate ratio, or efficiency index, goes up. This further supports the finding that pacing makes the patient's body more efficient than without pacing.

Figure 8:
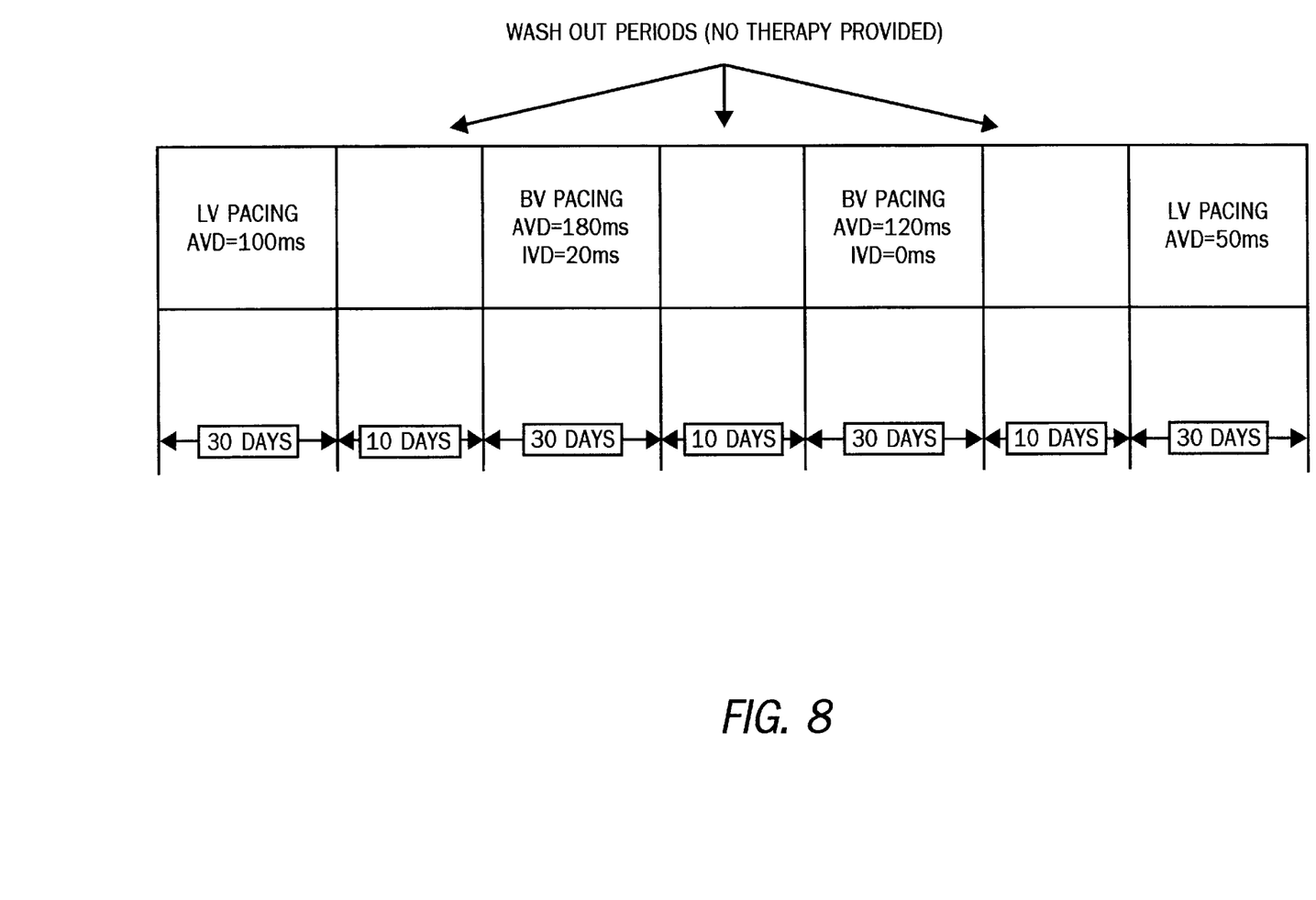
FIG. 8 is an example of a possible testing sequence that may be employed on CHF patients in the inventive method.

FIG. 8 shows an example therapy testing sequence that could have been used in the PATH-CHF study. The example therapy testing sequence includes four modes of pacing therapy, which are: 1) LV pacing at an AVD of 100 milliseconds; 2) LV pacing at an AVD of 50 milliseconds; 3) both RV and LV pacing ("BV," for both ventricles) at an AVD of 120 milliseconds with 0 milliseconds IVD; and 4) BV pacing with an AVD of 180 milliseconds and with a 20 milliseconds IVD. The default mode for this example testing sequence could be LV pacing at 150 ms. This example testing sequence includes wash-out periods of 10 days between the pacing periods. This is just one example of a therapy testing sequence that may be used.

Figure 9:
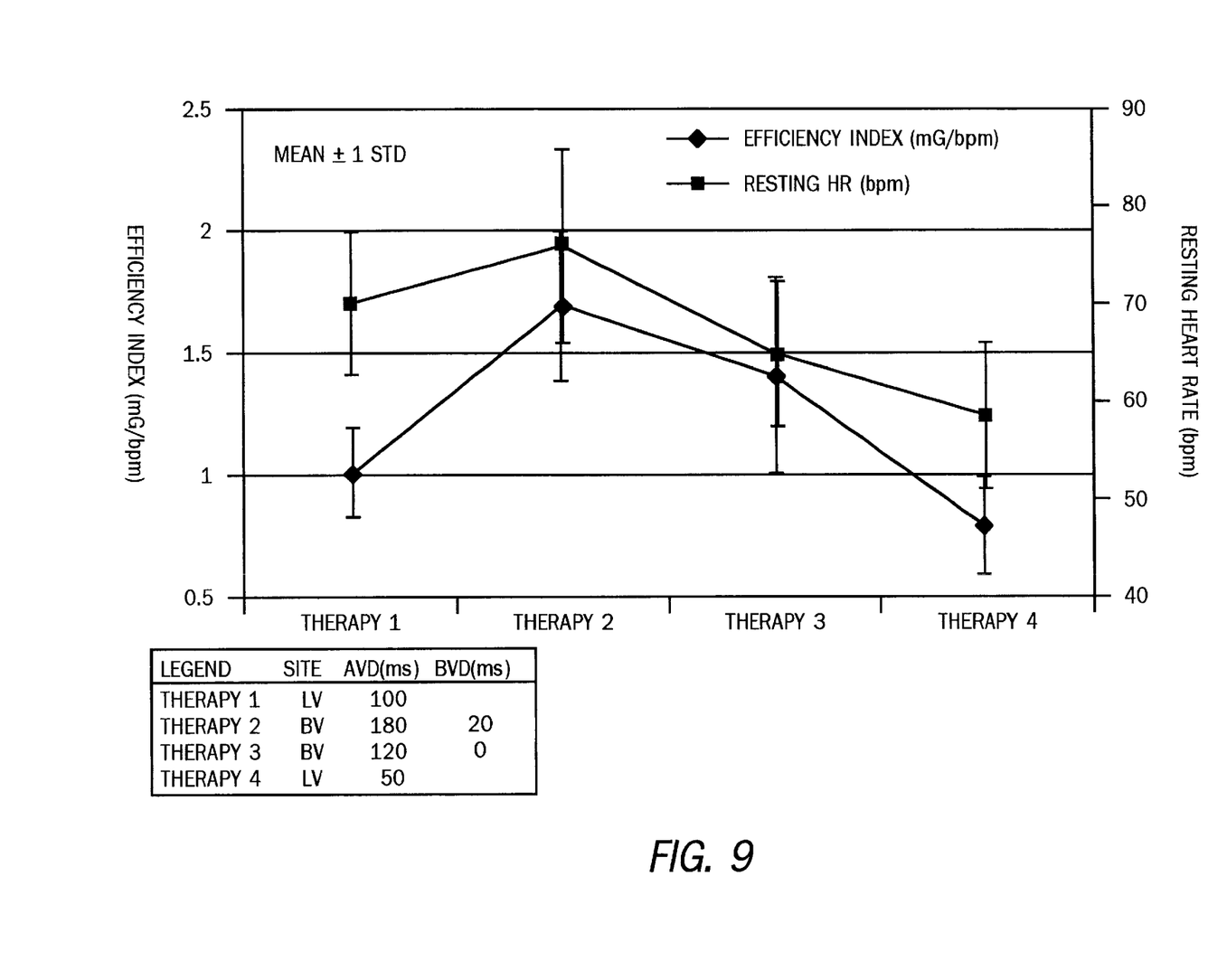
FIG. 9 is a sample programmer display of a graph of the efficiency index and resting heart rate averages for four different tested therapies.
Figure 10:
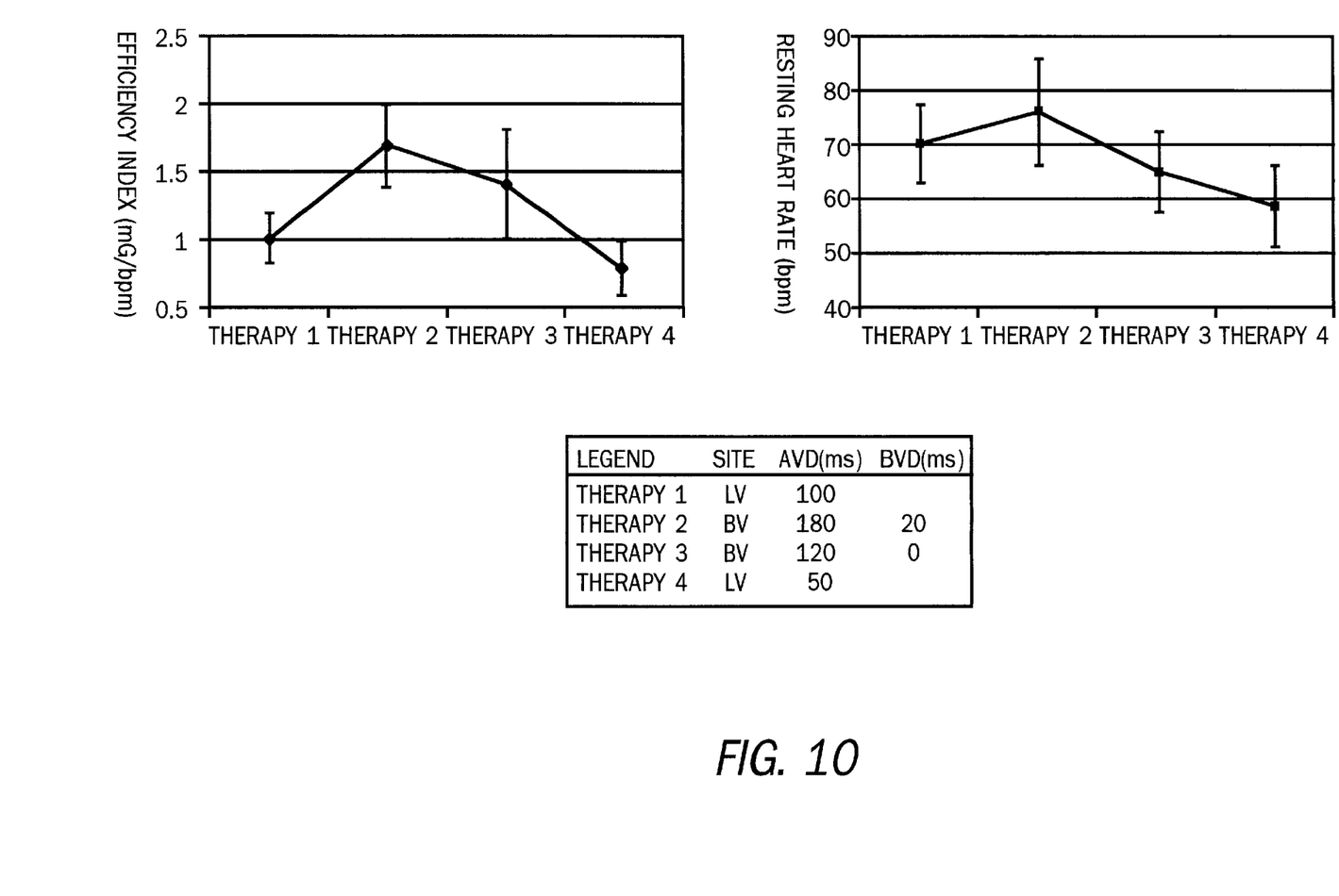
FIG. 10 is a second sample programmer display of the same values as those shown in FIG. 9, but in two separate graphs; one for the efficiency index and one for the resting heart rate.

FIGS. 9 and 10 show sample programmer displays for slopes and resting heart rates that may result from the four therapies, as described above in the possible testing sequence. These are, however, sample results and do not depict actual results measured from any particular patient. The first display in FIG. 9 shows the efficiency index and the resting heart rate values for the four different therapies on the same graph. FIG. 10 shows the efficiency index and resting heart values on two separate graphs. The figures also include legends that describe the therapies that were tested.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedure, can be accomplished without departing from the scope of the invention itself. Hence, the scope of the invention is to be determined from the appended claims.

What is claimed is:

1. An apparatus for carrying out the method of determining the best cardiac therapy for a patient, comprising a cardiac rhythm management device having:

(a) means for measuring acceleration due to body movement of the patient and producing an electrical signal proportional thereto;

(b) means for measuring heart rate of the patient and producing an electrical signal proportional thereto;

(c) means for storing the acceleration and heart rate measurements;

(d) means for calculating average values of acceleration and heart rate and ratios of acceleration to heart rate;

(e) means for comparing the values and the ratios from different cardiac therapies and determining which therapy is the best for the patient; and (f) means for displaying the values and the ratios.

2. The apparatus as defined in claim 1 wherein the means for measuring heart rate comprises electrodes on a pacing lead of said cardiac rhythm management device.

3. The apparatus defined in claim 1 wherein the means for measuring acceleration due to body movement is an accelerometer.

4. The apparatus as defined in claim 1 wherein the means for displaying values is a monitor.

5. The apparatus as defined in claim 1 wherein the means for storing, computing and comparing is a microprocessor.

6. The apparatus as defined in claim 5 and further comprising a pulse generator in an implantable cardiac rhythm management device that is signaled by the microprocessor to generate pulses at a determined rate.

7. An apparatus for carrying out the method of determining the best cardiac therapy for a patient, comprising:
(a) a pacing lead with at least one electrode for sensing heart rate and that outputs a proportional signal;
(b) a pulse generator that connects to said pacing lead and controls pacing of heart in the patient;
(c) an accelerometer that detects acceleration due to body movement of the patient and outputs a proportional signal;
(d) a microprocessor that connects to and controls said pulse generator, that connects to said accelerometer and receives a signal from said accelerometer, and that computes an efficiency index from heart rate and acceleration values for each therapy performed on the patient, and that is able to choose the best cardiac therapy, which is the one with the highest efficiency index, and that is able to signal said pulse generator to pace the heart of the patient with the best cardiac therapy.

8. The apparatus as defined in claim 7, and further comprising a monitor that is connected to said microprocessor and that displays heart rate and acceleration values and efficiency indexes for therapies that are tested on the patient.

9. A method of estimating efficiency of a patient's body, comprising the steps of:
(a) measuring acceleration due to body movement and heartrate of a patient while a first therapy is being administered;
(b) determining a first efficiency index based on a relationship between said heartrate and acceleration values determined in step (a);
(c) measuring acceleration due to body movement and heartrate of the patient while a second therapy is being administered;
(d) determining a second efficiency index based on a relationship between said heartrate and said acceleration values determined in step (c); and
(e) selecting one of the first or second therapies based upon a comparison of said first and second efficiency indices.

10. A method of estimating efficiency of a patient's body, comprising the steps of:
(a) defining a measuring period in which acceleration due to body movement and heartrate of a patient are measured;
(b) measuring acceleration due to body movement and heartrate of a patient for a plurality of predetermined time periods less than the defined measuring period within the defined measuring period;
(c) determining an efficiency index based on a relationship between the heartrate and acceleration values for each of the plurality of predetermined time periods; and
(d) computing an average of the efficiency indices determined during each of the plurality of predetermined time periods to determine an average efficiency index for the defined measuring period.

11. The method of estimating efficiency as in either of claim 9 or 10 and further comprising the step of outputting the efficiency index.

12. The method of estimating efficiency as in claim 11, wherein said outputting includes storing the efficiency index in a memory for later readout.

13. The method of estimating efficiency as in claim 11, wherein said outputting includes displaying the efficiency index in graph form.

14. The method as defined in claim 11, wherein said outputting includes displaying the efficiency index in table form.

15. A method for determining the best cardiac therapy for a patient, comprising the steps of:
(a) establishing a monitoring protocol defining:
(i) types of therapies that are to be tested on the patient;
(ii) number of therapies that are to be tested on the patient, and
(iii) a time period during which each therapy is to be tested on the patient;
(b) measuring values of acceleration due to body movement and heart rate of the patient during the defined time period of each of the defined therapies;
(c) calculating an average acceleration—heart rate ratio for each of the defined therapies;
(d) comparing the average acceleration—heart rate ratios of the defined therapies; and
(e) determining which of the defined therapies is the best, with the best therapy being the one with the highest average acceleration—heart rate ratio.

16. A method for determining the best cardiac therapy for a patient, said method comprising the steps of:
(a) providing a cardiac rhythm management device having a programmable microprocessor with a program defining a monitoring protocol including:
(i) types of cardiac pacing therapies that are to be tested on the patient;
(ii) a total time period during which the best cardiac therapy for the patient will be determined;
(iii) a plurality of first time periods within said total time period in which the pacing therapies are to be tested on the patient;
(iv) a plurality of wash-out periods between said first time periods in which no said pacing therapies are tested;
(v) a plurality of second time periods within said first time periods in which values of acceleration due to patient body movement and heart rate will be measured;
(b) measuring and storing average acceleration and heart rate values for each second time period within the first time period of a given pacing therapy;
(c) calculating and storing acceleration—heart rate ratio and resting heart rate value for each second time period during said given pacing therapy;
(d) repeating steps (b) and (c) for said given pacing therapy until said first time period has elapsed;
(e) calculating and storing average acceleration—heart rate ratio and average resting heart rate for said given pacing therapy;
(f) running the wash-out period after said given pacing therapy is tested;
(g) repeating steps (b), (c), (d), (e) and (f) for each pacing therapy that is to be tested;
(h) comparing the average acceleration—heart rate ratios and resting heart rate values from the pacing therapies that were tested; and
(i) determining the best pacing therapy for the patient, which is the one with the highest average acceleration—heart rate ratio.

17. The method as defined in claim 6 wherein said cardiac rhythm management device includes a closed loop switch that is enabled after the acceleration—heart rate ratios have been compared and said closed loop switch chooses and automatically programs the therapy with the highest acceleration—heart ratio.

* * * * *

UNITED STATES PATENT AND TRADEMARK OFFICE
CERTIFICATE OF CORRECTION

PATENT NO.    : 6,459,934 B1
DATED         : October 1, 2002
INVENTOR(S)   : Veerichetty Kadhiresan It is certified that error appears in the above-identified patent and that said Letters Patent is hereby corrected as shown below:

<u>Column 11,</u>
Line 1, change "6" to -- 16 --.

Signed and Sealed this

Twenty-fourth Day of December, 2002

JAMES E. ROGAN
*Director of the United States Patent and Trademark Office*